United States Patent [19]

Mikkelsen

[11] Plant 5,135

[45] Nov. 8, 1983

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 354,057

[22] Filed: Mar. 2, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Flare and characterized by its compact, superior self-branching habit; bright dark red to a dull red flower color depending on light conditions; variegated to wholly green foliage depending on light conditions; superior floriferousness; excellent keeping qualities for house plant use, and by its adaptability to varying use environments.

1 Drawing Figure

The present invention relates to a new and distinctive cultivar of Impatiens plant, botanically known as Impatiens, and known by the cultivar name Flare. The new cultivar was developed by me through controlled breeding in Ashtabula, Ohio. The seed parent was developed by crossing 78-836-2 (Mikkelsen) and the pollen parent 77-719-2 (Mikkelsen). Asexual reproduction of terminal or stem cuttings has shown that the unique features of this new impatiens are stabilized and are reproduced true to type in successive propagations.

The following characteristics distinguish Flare from both its parent varieties and other cultivated impatiens of this type known and used in the floriculture industry:

1. Compact, short, self-branching habit with faster growth than Red Planet, disclosed in U.S. Plant Pat. No. 4,690. Plant size is much larger than Red Planet under same growing conditions.

2. The new cultivar is easily flowered similar to Red Planet.

3. Flower color is bright dark red in screened light environments, becoming a somewhat dull red in full light conditions.

4. Foliage is variegated under full sun, but less so than Red Planet; leaves are nearly wholly green in screen or shaded areas. Flowering is also reduced in shaded areas. Foliage more durable than Red Planet.

5. Flare has good keeping qualities when used as a short term flowering house plant; Flare and Corona, disclosed in my pending application, will be valuable for hybridizing New Guinea Impatiens for house plants.

6. Flare is more floriferous than Red Planet and has slightly larger flowers.

7. Flare is ideal for hanging baskets mass bedding plant displays, and individual accent plants flowering all summer until killing frost.

8. The new cultivar is a greatly improved plant in all characteristics when compared to Red Planet.

The accompanying colored photograph taken in late September in full sun outdoors illustrates the overall appearance of Flare. The photo is a generally top perspective view of the plant and shows the colors as true as it is reasonably possible to obtain in a colored reproduction of this type.

The following is a detailed description of my new impatiens cultivar based on plants produced under commercial practices in Ashtabula, Ohio. The illustrated specimen was planted outside during the first week of June from a 4" pot. By the early part of September, the plant being shown measured 50 cm. diameter×25 cm. high. Color references are made to The Royal Horticultural Society Colour Chart except where general terms of ordinary dictionary significance are used.

Parentage: Mikkelsen seedling 78-836-2 × Mikkelsen seedling 77-719-2.

Propagation:

(A) *Stem cuttings.*—15 mm. long will develop to 4–5 cm. in 21–28 days.

(B) *Time to initiate root.*—8–10 days at 23° C. summer.

(C) *Time to initiate root.*—12–14 days at 20° C. winter.

Plant description:

(A) *Form.*—Low, compact, self-branching, symmetrically rounded plant, with red stems, close internodes, early flowering, and variegated foliage.

(B) *Habit of growth.*—Vigorous growth, compact, self-branching but average rate of growth.

(C) *Foliage description.*—A generally broader leaf than other hybrids of this general type; variegated, opposite until flowering; then in whorl of 5–7 leaves. (1) Size: 8–9 cm. long×4 cm. wide. (2) Shape: From lanceolate to ovate, apex acuminate, base acute. (3) Texture: Top surface rugose, underside glabrous. (4) Margin: Finely serrated. (5) Color: Young foliage, top side green 137A; under side yellow green 147-C; mature foliage, top side dull green between yellow green 147A and 139 in tone; under side green 137-C-D. Basal and mid-rib yellow variegation. (6) Venation: pinnate.

Flowering description:

(A) *Flowering habits.*—Flowering is early for New Guinea Impatiens, continuous and progressively advances up the stem as new leaf whorls develop. Under poor light conditions, buds may initiate but not develop, and abort.

(B) *Natural flowering season.*—Indeterminent, continous, usually one flower per leaf developing in whorls at terminals of stem.

(C) *Flower buds.*—Ellipsoidal, flowers perfect, red spur with throat originating from major sepal.

(D) *Flowers borne.*—Individual pedicels from whorl of leaves, flowering in succession as whorl develops, pedicels slightly extended above leaves giving a semi-compact placement of flowers.

(E) *Quantity of flowers.*—5–6 per whorl, with the number of flowers developing being directly dependent on quantity of light.

(F) *Petals.*—(1) Shape: Heart-shaped, top petal dominant, lower 2 separated. (2) Color, top side when opening under reduced light in winter, luminescent red 44A, fading to 44B-C; summer, full light, dull red 47A-B with light throat, fading to red 46B-C; under side in summer orange red 33A-B. (3) Number of petals: five (5). (4) Size of flowers: 5–6 cm. in diameter.

(G) *Reproductive organs.*—(1) Stamens: Five (5) in number. a. Anther shape: Hooded, color red to dark pink. b. Pollen color: Deep cream. (2) Pistils a. Stigma: Five (5) in number, segmented column-shaped, color tinted green. b. Style color: Nearly colorless. c. Ovaries: Five (5) in number, celled; size 5–6 mm. before fertilizing, color green. Capsule explosively dehiscent.

Disease resistance: Since origination of the cultivar there has been no observed infestation of diseases or insects other than botrytis petal rot outside in adverse wet cold weather.

I claim:

1. A new and distinct cultivar of impatiens plant known by the cultivar name Flare, as described and illustrated, and particularly characterized by its compact, superior self-branching habit; bright dark red to a dull red flower color depending on light conditions; variegated to wholly green foliage depending on light conditions; superior floriferousness; excellent keeping qualities for house plant use, and by its adaptability to varying use environments.

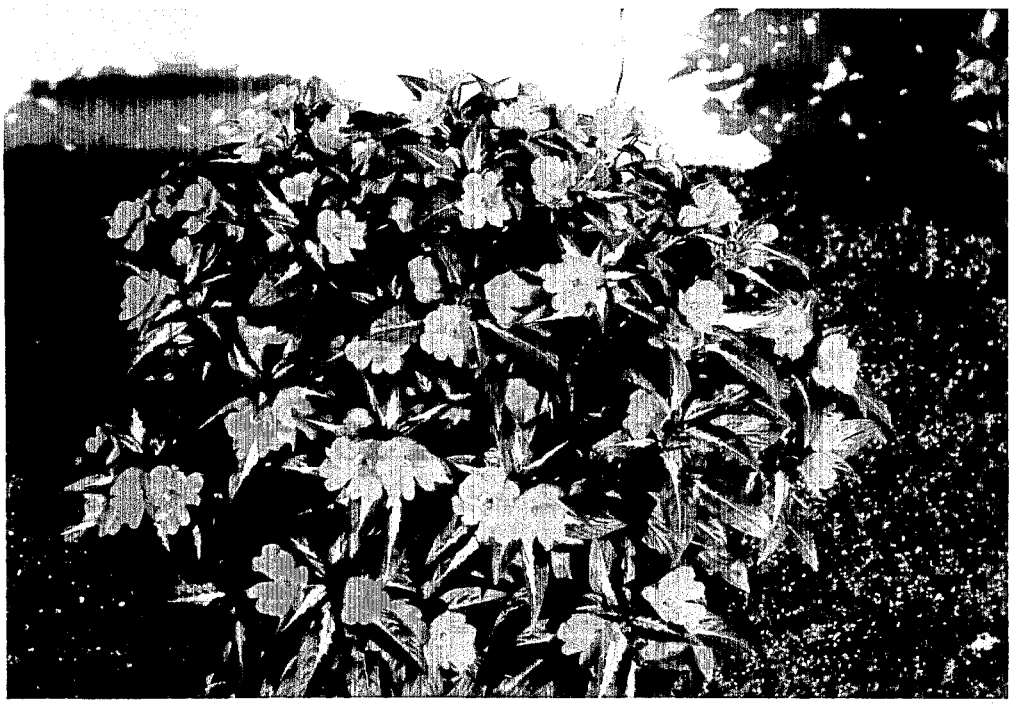

* * * * *